(12) United States Patent
Hessler et al.

(10) Patent No.: US 10,829,567 B2
(45) Date of Patent: Nov. 10, 2020

(54) MULTI-PHASE BACTERIALLY-SYNTHESIZED-NANO-CELLULOSE BIOMATERIALS AND METHOD FOR PRODUCING THE SAME

(71) Applicant: JENACELL GMBH, Jena (DE)

(72) Inventors: Nadine Hessler, Mengersgereuth-Hammern (DE); Barno Baumbach, Jena (DE); Dieter Klemm, Weimar (DE)

(73) Assignee: JENACELL GMBH, Jena (DE)

( * ) Notice: Subject to any disclaimer, the term of this patent is extended or adjusted under 35 U.S.C. 154(b) by 771 days.

(21) Appl. No.: 14/597,235

(22) Filed: Jan. 15, 2015

(65) Prior Publication Data

US 2015/0225486 A1 Aug. 13, 2015

Related U.S. Application Data

(63) Continuation of application No. 13/634,788, filed as application No. PCT/DE2011/000269 on Mar. 15, 2011, now abandoned.

(30) Foreign Application Priority Data

Mar. 19, 2010 (DE) .................. 10 2010 012 437

(51) Int. Cl.
*C08B 15/10* (2006.01)
*C12P 19/04* (2006.01)
*A61L 27/48* (2006.01)

(52) U.S. Cl.
CPC .............. *C08B 15/10* (2013.01); *A61L 27/48* (2013.01); *C12P 19/04* (2013.01); *A61L 2400/12* (2013.01); *Y10T 428/31978* (2015.04)

(58) Field of Classification Search
None
See application file for complete search history.

(56) References Cited

U.S. PATENT DOCUMENTS

| 4,655,758 A | 4/1987 | Ring |
| 4,950,597 A | 8/1990 | Saxena |
| 4,954,439 A | 9/1990 | Brown, Jr. |
| 5,472,859 A | 12/1995 | Brown, Jr. |
| 6,153,413 A * | 11/2000 | Watanabe ............... C12P 19/04 435/101 |
| 6,429,002 B1 | 8/2002 | Ben-Bassat et al. |
| 2004/0175407 A1 * | 9/2004 | McDaniel ................ A62D 3/02 424/423 |

(Continued)

FOREIGN PATENT DOCUMENTS

| CN | 1850302 A | 10/2006 |
| CN | 1966093 A | 5/2007 |

(Continued)

OTHER PUBLICATIONS

Apr. 15, 2005, Zhang et al, Royal Society of Chemistry, 2005, Chem Commun 2005, 2735-3737.

(Continued)

*Primary Examiner* — Chinessa T. Golden
(74) *Attorney, Agent, or Firm* — Barnes & Thornburg LLP; Ryan L. Marshall

(57) ABSTRACT

Multi-phase biomaterials based on bacterially synthesized nanocellulose and method for producing same.

86 Claims, 3 Drawing Sheets

(56) References Cited

U.S. PATENT DOCUMENTS

| | | | |
|---|---|---|---|
| 2006/0115457 A1* | 6/2006 | Hnojewyj | A61K 9/0024 |
| | | | 424/93.7 |
| 2007/0053960 A1 | 3/2007 | Brown et al. | |
| 2009/0209897 A1 | 8/2009 | Limaye et al. | |
| 2009/0269406 A1* | 10/2009 | Panitch | A61K 8/042 |
| | | | 424/487 |
| 2010/0029584 A1* | 2/2010 | Merizzi | C12P 19/04 |
| | | | 514/57 |
| 2013/0004784 A1 | 1/2013 | Hessler | |

FOREIGN PATENT DOCUMENTS

| | | |
|---|---|---|
| CN | 101288778 A | 10/2008 |
| CN | 101509026 A | 8/2009 |
| JP | 2009-24274 | 2/2009 |
| JP | 2009-77752 | 4/2009 |
| WO | 2007027849 A2 | 3/2007 |

OTHER PUBLICATIONS

Biocomposites produced from plant microact bundles with a nanometer until web-like network H. Yano, et al. Journal of Materials Science 39 (2004) 1635-4638.

Akira Seto et al, Applied Microbial and Cell Phys, 2006, 73, 915-921.

Nov. 16, 2004 Biomechanical properties of high toughness double network hydrogels Kazunori Yasuda, et al. Biomaterials 26 (2005) 4468-4475.

Oct. 31, 1994 Enhancement of Bacterial Cellulose Productivity and Preparation of Branced Polysaccharide-Bacterial Cellulose Composite by Co-cultivation of Acerobacter Species; K. Tajima, et al. SEN-I GAKXAISHI vol. 51, No. 7 (1995) 323-332.

Mar. 19, 2002 Inclusion of solid particles in bacterial cellulose G. Serafica, et al. Appl Microbiol Biotechnol (2002) 58 756-760.

Nobuo Sakairi et al, Carbohydrate Polymers, 35, 1998, 233-237.

Koon-Yang Lee et al, Composites Science and Technology, 69, 2009, 2724-2733.

May 22, 2009 Alteration of bacterial nanocellulose structure by in situ modification using polyethylene glycol and carbohydrate additives. Nadine Hessler, at al. Cellulose (2009) 16 899-910.

High Mechanical Strength Double-Network Hydrogel with Bacterial Cellulose, Atsushi Nakayama, et al. Advance Functional Materials 2004, 14, No. 11, Nov. 24-28.

Alteration of In Vivo Cellulose Ribbon Assembly by Carboxymethylcellulose and Other Cellulose Derivatives, Candace Haigler, et al. The journal of Cell Biology—vol. 94 Jul. 1982 64-69.

Aug. 20, 2002 Palladium-bacterial cellulose membranes for fuel cells, Barbara R. Evans, et al. Biosensors and Bioelectronics 18 (2003) 917-923.

Dec. 15, 2004 Pervaporative separation of ethanol/water azeotrope using a novel chitosan-impregnated bacterial cellulose membrane and chitosan-poly (vinyl alcohol) blends, Vinita Dubey, et al, journal of Membrane Science 251 (2005) 131-136.

Aug. 17, 2009 Mechanical characteristics of artificial cell walls Justyna Cybulska, et al. Journal of Food Engineering 96, 2010, 287.

Pervaporation of binary water-ethanol mixtures through bacterial cellulose membrane Vinita Dubey, et al. Separation and Purification Technology 27 .(2002) 163-171.

Nov. 8, 2005 Surface functionalization of cellulose fibers with titanium dioxide nanoparticies and their combined bactericidal activities, Walid A. Daoud. et al. Surface Science 599 (2005) 69-75.

Jul. 16, 2001 Structure of Acetobacter cellulose composites in the hydrated state Owen M. Astley, et al. International Journal of Biological Macromolecules 29 (2001) 193-202.

Aug. 30, 2006 Nanocelluloses as Innovative Polymers in Research and Application Dieter Klemm, et at. Adv Poiym Sci 2006. 1-48.

Written opinion for PCT Application No. PCT/DE2011/000269, dated Sep. 19, 2012.

Bacterial Cellulose Production and its Industrial Applications,Keshk, Bioprocessing & Biotechniques; vol. 4; 2014.

\* cited by examiner

MULTI-PHASE BACTERIALLY-SYNTHESIZED-NANO-CELLULOSE BIOMATERIALS AND METHOD FOR PRODUCING THE SAME

FIELD OF THE INVENTION

The present invention relates to multi-phase biomaterials and in particular to such biomaterials based on bacterially synthesized nanocellulose, and a method for producing and using same.

BACKGROUND OF THE INVENTION

It is general knowledge that homogeneous or multi-phase biomaterials based on bacterially synthesized nanocellulose (BNC) can be influenced by modifying said material after its synthesis (post-modification) (K.-Y. Lee, J. J. Maker, A. Bismarck: Surface fictionalisation of bacterial cellulose as the route to produce green polylactide nanocomposites with improved properties, Composites Science and Technology (2009), 69(15-16), 2724-2733; D. Klemm, D. Schumann, F. Kramer, N. He[beta]ler, M. Hornung, H.-P. Schmauder, S. Marsch: Nanocelluloses as Innovative Polymers in Research and Application. Advances in Polymer Science (2006), 205 (Polysaccharides II), 49-96).

However, it is also possible to perform an in situ modification already with the synthesis of the bio-technological cultivation process (H. Wang, F. Guan, X. Ma, S. Ren: Production and performance determination of modified bacterial cellulose, Shipin Keji (2009), (5), 28-31; N. Hessler, D. Klemm: Alteration of bacterial nanocellulose structure by in situ modification using polyethylene glycol and carbohydrate additives, Cellulose (Dordrecht, Netherlands) (2009), 16(5), 899-910; D. Klemm, D. Schumann, F. Kramer, N. He[beta]ler, M. Hornung, H.-P. Schmauder, S. Marsch: Nanocelluloses as Innovative Polymers in Research and Application. Advances in Polymer Science (2006), 205 (Polysaccharides II), 49-96).

In this case, different addition agents are added to the culture medium during the biosynthesis (e.g, M. Seifert: Modifizierung der Struktur von Bakteriencellulose durch die Zusammenstellung des Nahrmediums bei der Kultivierung von *Acetobacter xylinum*, [Modification of the structure of bacterial cellulose by composing the cultural medium in the cultivation of *Acetobacter xylinum*], doctoral thesis, Friedrich-Schiller-University Jena, Germany, 2004; O. M. Astley, E. Chanliaud, A. M. Donald, M. J. Gidley: Structure of Acetobacter cellulose composites in the hydrated state, International journal of biological macromolecules (2001), 29/3, 193-202; N. Sakairi, H. Asano, M. Ogawa, N. Nishi, S. Tokura: A method for direct harvest of bacterial cellulose filaments during continuous cultivation of Acetobacter xylinum. Carbohydrate Polymers (1998), 35/3-4, 233-7; C. H. Haigler, A. R. White, R. M. Brown Jr., K. M. Cooper: Alteration of In Vivo Cellulose Ribbon Assembly by Carboxymethylcellulose and Other Cellulose Derivative, J Cell Biology (1982), 94, 64-9).

According to this reference, the addition of carboxymethyl cellulose (CMC) and methyl cellulose (MC) has huge effects on the BNC network. Due to their embedding, both additives have an influence on the pore system and the properties resulting from it, e.g. elasticity, water retention capacity, filter function, and thus novel BNC materials are produced (O. M. Astley, E. Chanliaud, A. M. Donald, M. J. Gidley: Structure of Acetobacter cellulose composites in the hydrated state, International journal of biological macromolecules (2001), 29/3, 193-202; N. Sakairi, H. Asano, M. Ogawa, N. Nishi, S. Tokura: A method for direct harvest of bacterial cellulose filaments during continuous cultivation of Acetobacter xylinum. Carbohydrate Polymers (1998), 35/3-4, 233-7; C. H. Haigler, A. R. White, R. M. Brown Jr., K. M. Cooper: Alteration of In Vivo Cellulose Ribbon Assembly by Carboxymethylcellulose and Other Cellulose Derivative, J Cell Biology (1982), 94, 64-9).

Moreover, the addition of vegetable cell wall accompanying components, such as xyloglucan or pectin, to the culture medium during the BNC biosynthesis was found to partially imitate structural relationships of native cellulose and to analyze formation of same in detail (J. Cybulska, E. Vanstreels, Q. T. Ho, C. M. Courtin, V. Van Craeyveld, B. Nicolai, A. Zdunek, K. Konstankiewicz: Mechanical characteristics of artificial cell walls, Journal of Food Engineering (2009), 96(2), 287-294).

Unlike water-soluble compounds, solids can also be given as additives to the culture medium during the biosynthesis and are integrated in the produced BNC network. Whereas Udhardt (U. Udhardt: Synthese, Eigenschaften and Strukturdesign von Bakteriencellulose mit speziellem Anwendungspotential von BASYC®-Implantaten in der Mikrochirurgie [Synthesis, properties and structural design of bacterial cellulose with a specific application potential of BASYC® implants in microsurgery], doctoral thesis, Friedrich Schiller University Jena, Germany, 2004) described an integration of crystal balls or an integration of silica gel and inorganic salts (calcium carbonate) into the BNC network, Serafica et al. (G. Serafica, R. Mormino, Bungay: Inclusion of solid particles in bacterial cellulose, Applied Microbiology and Biotechnology (2002), 58/6, 756-60) mainly reported about the integration of metals (aluminum) or metal oxide (ferric oxide) particles.

However, these in situ methods have a number of disadvantages; without wishing to be limited by a closed list, they require additives to produce novel biomaterials on BNC basis. Thus, the structure and the properties combined with it can only be controlled by using water-soluble organic, inorganic substances or polymers and solid particles.

Furthermore, in contrast to pure BNC, BNC with the integrated additives may cause possible allergic reactions if they are used as medical products.

In the post modification method, a modification of the BNC and the production of homogenous or multiphase materials are achieved by integrating organic or inorganic substances after the cultivation (B. R. Evans, H. O'Neil, M. Hugh, V. P. Malyvanh, I. Lee, J. Woodward: Palladium-bacterial cellulose membranes for fuel cells, Biosensors & Bioelectronics (2003), 18/7, 917-23; B. R. Evans, H. M. O'Neill, E. Greenbaum: Electron Transfer by Enzymes and Photosynthetic Proteins Immobilized in Polysaccharide Composites, Abstracts, 57th Southeast/61st Southwest Joint Regional Meeting of the American Chemical Society, Memphis, Tenn., United States, Nov. 1-4, 2005; W. A. Daoud, J. H. Xin, Y.-H.Zhang; Surface functionalization of cellulose fibers with titanium dioxide nanoparticles and their combined bactericidal activities, Surface Science (2005), 599(1-3), 69-75; D. Zhang, L. Qi: Synthesis of mesoporous titania networks consisting of anatase nanowires by templating of bacterial cellulose membranes, Chem. Commun. (2005), 21, 2735-7).

By means of this method a multitude of BNC variations have already been realized, e.g. by the use of different types of monomers and synthetic polymers (H. Yano, S. Nakahara: Bio-composites produced from plant microfiber bundles with a nanometer unit web-like network, Journal of Materials Science (2004), 39/5, 1635-8; V. Dubey, L. K. Pandey, C. Saxena: Pervaporative separation of ethanol/water azeotrope using a novel chitosan-impregnated bacterial cellulose membrane and chitosan-poly(vinyl alcohol) blends, Journal of Membrane Science (2005), 251(1-2), 131-136; V. Dubey, C. Saxena, L. Singh, K. V. Ramana, R. S. Chauhan: Pervaporation of binary water-ethanol mixtures through bacterial cellulose membrane, Separation and Purification Technology (2002), 27/2, 163-71; W. A. Daoud, J. H. Xin, Y.-H. Zhang: Surface functionalization of cellulose fibers with titanium dioxide nanoparticles and their combined bactericidal activities, Surface Science (2005), 599(1-3), 69-75), structure-forming polymers, e.g. PVA (T. Wan, Y. Zhu: Preparation of bacterial cellulose/poly(vinyl alcohol) composite gels, Faming Zhuanli Shenqing Gongkai Shuomingshu CN 101570616, 2009), gelatin (K. Yasuda, J. P. Gong, Y. Katsuyama, A. Nakayama, Y. Tanabe, E. Kondo, M. Ueno, Y. Osada; Biomechanical properties of high-toughness double network hydrogels, Biomaterials (2005), 26/2, 4468-75; A. Nakayama, A. Kakugo, J. P. Gong, Y. Osada, M. Takai, T. Erata, S. Kawano: High mechanical strength double-network hydrogel with bacterial cellulose, Advanced Functional Materials (2004), 14/11, 1124-8) and by inorganic substances e.g. calium salts, metals, metal oxides (B. R. Evans, H. O'Neil, M. Hugh, V. P. Malyvanh, I. Lee, J. Woodward: Palladium-bacterial cellulose membranes for fuel cells, Biosensors & Bioelectronics (2003), 18/7, 917-23; B. R. Evans, H. M. O'Neill, E. Greenbaum: Electron Transfer by Enzymes and Photosynthetic Proteins Immobilized in Polysaccharide Composites, Abstracts, 57th Southeast/61st Southwest Joint Regional Meeting of the American Chemical Society, Memphis, Tenn., United States, Nov. 1-4, 2005; Daoud, J. H. Xin, Y.-H. Zhang: Surface functionalization of cellulose fibers with titanium dioxide nanoparticles and their combined bactericidal activities, Surface Science (2005), 599(1-3), 69-75; D. Zhang, L. Qi: Synthesis of mesoporous titania networks consisting of anatase nanowires by templating of bacterial cellulose membranes, Chem. Commun. (2005), 21, 2735-7).

However, without wishing to be limited by a closed list, these methods have a number of disadvantages, including the fact that they require two production steps (synthesis of BNC and its modification) for developing novel BNC. Moreover, the post modification modifies the BNC partly to such an extent that the unique structure and consequently the excellent properties are lost. In addition to this, these methods require the disadvantageous use of additives, too.

Another proposed solution for producing new BNC material is based on the common cultivation of bacteria of different strains, although such solutions related only to supporting better production of a single BNC material. Thus, A. Seto et al. (A. Seto, Y. Saito, M. Matsushige, H. Kobayashi, Y. Sasaki, N. Tonouchi, I. Tsuchida, F. Yoshinaga, K. Ueda, T. Beppu: Effective cellulose production by a coculture of *Gluconacetobacter xylinus* and *Lactobacillus mali*, Applied Microbiology and Biotechnology (2006), 73(4), 915-921), C. Choi et al. (KR 2002/067226) and H. Seto et al. (JP 10201495) demonstrated that the yield of synthesized cellulose could be optimized by co-cultivating a cellulose-forming bacterial strain (*Acetobacter xylinum* (st-60-12)) with a lactobacillus strain (*Lactobacillus mali* (st-20)). This effect is mainly due to the metabolites of the lactobacillus strain, such as acetic acid, that support the biosynthesis of cellulose (A. Seto, Y. Saito, M. Matsushige, H. Kobayashi, Y. Sasaki, N. Tonouchi, T. Tsuchida, F. Yoshinaga, K. Ueda, T. Beppu: Effective cellulose production by a coculture of *Gluconacetobacter xylinus* and *Lactobacillus mali*, Applied Microbiology and Biotechnology (2006), 73(4), 915-921; KR 2002/067226; JP 10201495).

In contrast to the aforementioned method, the co-cultivation of *Acetobacter aceti* subsp. *xylinum* (NCI 1005) with the strains ATCC 10245 or NCI 1051 led to the increase of the respective polymer synthesis. Thus, the additional cellulose production and its subsequent decomposition cause, on the one hand, the increase of the nutrients in the culture solution and consequently an increased yield of the polymers. On the other hand, the presence of cellulose in the culture solution made the formation of water-soluble branched polysaccharides possible (K. Tajima, H. Ito, M. Fujiwara, M. Takai, J. Hayashi: Enhancement of bacterial cellulose productivity and preparation of branched polysaccharide-bacterial cellulose composite by co-cultivation of *Acetobacter* species, Sen'i Gakkaishi (1995), 51(7), 323-32; K. Tajima, M. Fujiwara, M. Takai: Biological control of cellulose. Macromolecular Symposia (1995), 99 (Functional Polysaccharides), 149-55).

However, one of ordinary skill in the art would typically use co-cultivation methods that provide increased yield of cellulose or that provide a composite formation, and would always cultivate a single cellulose-producing bacterial strain known for cellulose synthesis in order to produce any given BNC. Modifications of the BNC properties are exclusively caused by additives that are added during the cultivation process or after it and settle in the BNC structure. Moreover, the range of structures of such multi-phase biomaterial systems is strongly restricted because only homogeneous structures can be obtained through such a process.

SUMMARY OF THE INVENTION

The present invention, in at least some embodiments, relates to biomaterials based on bacterially-synthesized nanocellulose which are co-synthesized from at least two different cellulose-producing bacterial strains to form a plurality, i.e. at least two, different bacterial cellulose networks in a common culture medium. Optionally and preferably, the properties of the bacterial cellulose are not achieved by deliberately added additives or composite formations created during synthesis with a single bacterial strain, but rather by the controlled generation of the synthesized phase system consisting of a plurality of different bacterial cellulose networks. Such bacterial cellulose networks, which differ from each other in their molecular and/or supra-molecular structure in particular, may optionally be synthesized, for example, as a combined homogeneous phase system and thus generate a common homogeneous phase of the biomaterial. Such cultivation of a plurality different bacterial strains in order to influence the structure and properties of BNC by forming a multiphase BNC has not been disclosed.

Without wishing to be limited by a closed list, such materials are suitable for a broad range of applications, for example in medicine (wound dressings, great variety of implants), in engineering (membranes, foils, barrier layers) and in food industry (zero-calorie nutrition, packaging) due to highly versatile determinable structures and material properties.

The biomaterials are optionally and preferably designed according to a method for obtaining defined structures and properties, which, without wishing to be limited by a closed list, are optionally and preferably selected from the group consisting of mechanical strengths, elasticity, transparency and water balance, particularly the capability to re-expand appropriately and completely after drying, as well as socalled filter/membrane functions (permeability), scaffold-properties (pore system, surface characteristics, colonization by cells) and bio-compatibility (body compatibility, endothelialization, immigration of body's own cells, permanent integration into the body). Non-limiting specific examples of such properties include high water content with gelatinous, soft consistency and dense material structure of high strength. Again, optionally and preferably such structures and properties are obtained without requiring disadvantageous additives or composite formations produced in the synthesis with them.

Without wishing to be limited by a closed list, one aspect of the present invention, in at least some embodiments, is to create multi-phase biomaterials based on bacterially synthesized nanocellulose without required additives and composite formations, whereby the bacterial cellulose properties of said biomaterials can be specifically influenced in very wide limits in the synthesis process.

According to at least some embodiments, optionally the at least two different bacterial cellulose networks have the structure of a layered phase system comprising joined BNC-network-specific separate single phases. A linked formation of the aforementioned phase systems can also be generated if the at least two different bacterial cellulose networks are formed as a layered phase system consisting of at least one combined homogeneous phase and of at least one single phase.

The structure and properties of the BNC materials can optionally and preferably be specifically defined by the volumetric ratio of the aqueous cell dispersions of the bacterial strains used and can be controlled in the synthesis in a "tailored" manner. Such "tailoring" can be applied to all structures and properties that are relevant for the application of BNC materials according to a variety of applications, optionally including but not limited to a wet or dried (hot-pressed, air- or freeze-dried) form, for example and without limitation, in medicine (wound dressings, implants), in technology (membranes, foils, barrier layers) and in food industry (zero-calorie nutrition, packaging). This refers to the control of the mechanical strength, elasticity, permeability, transparency and water balance as well as of scaffold-properties (pore system, surface characteristics, colonization by cells) and bio-compatibility (body compatibility, endothelialization, immigration of body's own cells, permanent integration into the body).

Without wishing to be limited by a closed list, in the synthesis process, the structure and properties of the BNC materials can be influenced by the variation of the cultivation (combination of the bacterial strains before or after the inoculation) of the corresponding cellulose-producing bacterial strains, by the use of different culture media or by the use of different cultivation parameters (temperature, duration, volume, cultivation vessels).

According to at least some embodiments, the BNC materials comprise materials produced by bacterial strains that generate cellulose-like structures on the basis of modified C-sources (carbon sources), e.g. the use of N-acetyl glucosamine or glucosamine as C-source.

Preferably, the multi-phase biomaterials are translucent. More preferably, the multi-phase biomaterials are transparent. By "transparent" it is meant that a majority of visible light passes through the biomaterial. Transparent BNC biomaterials are known. However, so far transparent BNC biomaterials were obtainable only up to a thickness of about 2 mm. In contrast, according to at least some embodiments, the BNC multi-phase biomaterials are preferably transparent up to a thickness of about 3 mm, more preferably up to a thickness of about 5 mm, more preferably up to a thickness of about 7 mm, more preferably up to a thickness of about 10 mm, more preferably up to a thickness of about 15 mm, more preferably up to a thickness of about 20 mm, more preferably up to a thickness of about 30 mm, more preferably up to a thickness of about 50 mm. It has presently been found that particularly transparent multi-phase biomaterials may be obtained in case the at least two different bacterial cellulose networks are formed as a combined homogeneous phase system.

Without wishing to be limited by a closed list, the transparent multi-phase biomaterials are particularly advantageous as wound dressings. The transparency of the inventive biomaterials enables the visual inspection of the wounds without the need to remove the protective wound dressing. The fact that transparent wound dressings with a thickness of more than 2 mm may be obtained according to the present invention is particularly advantageous for wound dressings for severe burns (e.g. second- or third-degree burns). Such burns usually produce a high amount of exudates that have to be absorbed by the wound dressing.

The previously known thin wound dressings with a thickness of 2 mm or less have a very limited potential of absorbing the exudates because of their low solids content. Theoretically, the solids content may be increased by removal of liquid. However, removal of liquid results in a decrease of the thickness of the biomaterial. The previously known biomaterials are already very thin. A further decrease of the thickness by the removal of liquid would lead to biomaterials that are too thin for being used as wound dressings. Therefore, such thin biomaterials are not suitable for increasing the solids content by removal of liquid. Consequently, art known wound dressings with low solids content do have to be exchanged frequently in order for the exudates to be absorbed sufficiently. Thus, the advantage of being transparent is rendered void by the limited solids content of such prior art wound dressings at a given thickness.

In contrast, the transparent multi-phase biomaterials according to various embodiments of the present invention may be obtained with much higher thickness. Consequently, the solids content of the multi-phase biomaterials may be increased by removal of liquid because a sufficient thickness of the biomaterials remains after removal of liquid due to the increased initial thickness of the biomaterials. Thus, according to at least some embodiments, the present invention provides transparent wound dressings of increased solids content that enable absorption of substantially more volume of exudates as compared to previously known transparent wound dressings so that an exchange of the wound dressing is required substantially less frequently.

Preferably and according to at least some embodiments, the transparent multi-phase biomaterial of the present invention has a solids content of at least 1%, more preferably at least 2%, more preferably at least 3%, more preferably at least 5%, more preferably at least 6%, more preferably at least 8%, more preferably at least 10%, more preferably at least 15%, more preferably at least 20%, more preferably at least 25% at a thickness of the biomaterial of about 2 mm. As described herein, the solids content is calculated as the ratio of the weight of the solid components of the biomaterials (mainly BNC) to the total weight of the biomaterials (solid and liquid components combined).

Optionally and preferably, the multi-phase biomaterials have a tensile strength in the native wet state of at least 0.1 MPa, more preferably at least 0.15 MPa, more preferably at least 0.2 MPa. Optionally and preferably, the multi-phase biomaterials have a tensile strength in the native wet state of at most 0.9 MPa, more preferably at most 0.7 MPa, more preferably at most 0.5 MPa. Preferably, the multi-phase biomaterials have a tensile strength in the wet state of from 0.2 MPa to 0.5 MPa.

Preferably, in the native wet state the multi-phase biomaterials have a solids content of from about 0.5% to about 1.5%, more preferably a solids content of about 1%.

Preferably and according to at least some embodiments, the multi-phase biomaterials have a water absorption capacity (WAC) of at least 80%, more preferably at least 120%, more preferably at least 150%. As described herein, the water absorption capacity is calculated by the following formula WAC=mass(wet)/mass(dry)*100%. Preferably, the multi-phase biomaterials have a water absorption capacity (WAC) of at most 300%, more preferably at most 250%, more preferably at most 200%. Optionally and preferably, the multi-phase biomaterials have a water absorption capacity (WAC) of from 150% to 200%.

Preferably, the multi-phase biomaterials have a moist vapor transmission rate in the wet state of at least 100 g/(m$^2$*24 h), more preferably at least 200 g/(m$^2$*24 h), more preferably at least 500 g/(m$^2$*24 h). Preferably, the multi-phase biomaterials have a moist vapor transmission rate in the wet state of at most 3000 g/(m$^2$*24 h), more preferably at most 2000 g/(m$^2$*24 h), more preferably at most 1000 g/(m$^2$*24 h). Particularly preferably, the multi-phase biomaterials have a moist vapor transmission rate in the wet state of from 500 g/(m$^2$*24 h) to 1000 g/(m$^2$*24 h).

According to at least some embodiments of the present invention, the at least two different BNC networks preferably differ in their molecular structure. Without wishing to be limited by a closed list, the different BNC networks may optionally differ with regard to the degree of polymerization ($DP_n$), the polydispersity index (PDI) or with regard to both $DP_n$ and PDI. Preferably, the different BNC networks differ with regard to both $DP_n$ and PDI.

The degree of polymerization is the average number of monomeric units in the BNC polymers of a specific BNC network. It can be expressed as the ratio of the number-average molecular weight of the respective BNC polymers to the molecular weight of the monomeric unit.

The polydispersity index is a measure of the heterogeneity of the molecular mass distribution of the BNC polymers of a respective BNC network. It is calculated as the ratio of the weight-average molecular weight to the number-average molecular weight of the respective BNC polymers. Higher PDI values indicate a broader molecular weight distribution of the BNC polymers of a BNC network.

According to at least some embodiments, preferably at least one BNC network is characterized by a $DP_n$ of at least 4000, more preferably at least 6000, more preferably at least 8000. Preferably, at least one BNC network of the multi-phase biomaterials has a $DP_n$ of at most 2000, more preferably at most 1000, more preferably at most 500. Preferably, the $DP_n$ of the BNC network with the highest $DP_n$ in a particular multi-phase biomaterial of the present invention is higher by a factor of at least 2, more preferably at least 5 as compared to the $DP_n$ of the BNC network with the lowest $DP_n$ in the same multi-phase biomaterial.

According to at least some embodiments, preferably at least one BNC network is characterized by a PDI of at least 1.5, more preferably at least 1.7, more preferably at least 2.0. Preferably, all BNC networks of the multi-phase biomaterials have a PDI of at most 8, more preferably at most 6, more preferably at most 4. Preferably, the PDI of the BNC network with the highest PDI in a particular multi-phase biomaterial of the present invention is higher by a factor of at least 1.5, more preferably at least 2, more preferably at least 3 as compared to the PDI of the BNC network with the lowest PDI in the same multi-phase biomaterial.

When two BNC networks of a particular multi-phase biomaterial of the present invention are compared, optionally and preferably the BNC network with the higher PDI has a lower $DP_n$ as compared to the BNC network with the lower PDI.

According to at least some embodiments of the present invention, the at least two different BNC networks differ in their supra-molecular structure. Preferably, the at least two different BNC networks differ in their degree of crystallinity. The degree of crystallinity is preferably determined by NMR spectroscopy. According to at least some embodiments, preferably at least one BNC network is characterized by a degree of crystallinity of at least 55%, more preferably at least 60%, more preferably at least 65%. Preferably, all BNC networks of the multi-phase biomaterials have a degree of crystallinity of at most 95%, more preferably at most 80%, more preferably at most 70%. Preferably, the degree of crystallinity of the BNC network with the highest degree of crystallinity in a particular multi-phase biomaterial is higher by a factor of at least 1.2, more preferably at least 1.5, more preferably at least 2 as compared to the degree of crystallinity of the BNC network with the lowest degree of crystallinity in the same multi-phase biomaterial.

The at least two different BNC networks may also optionally differ with regard to the thickness of the microfibrils.

The at least two different BNC networks may also optionally differ with regard to their pore size. The pore size can be expressed as the average cross sectional area of the pores. The average cross sectional pore area may be determined by scanning electron microscopy. According to at least some embodiments, preferably at least one BNC network is characterized by an average cross sectional pore area of at least 15 µm$^2$, more preferably at least 20 µm$^2$, more preferably at least 25 µm$^2$. Preferably, all BNC networks of the multi-phase biomaterials have an average cross sectional pore area of at most 50 µm$^2$, more preferably at most 40 µm$^2$, more preferably at most 30 µm$^2$. Preferably, the average cross sectional pore area of the BNC network with the highest average cross sectional pore area in a particular multi-phase biomaterial is higher by a factor of at least 1.2, more preferably at least 1.5, more preferably at least 2 as compared to the average cross sectional pore area of the BNC network with the lowest average cross sectional pore area in the same multi-phase biomaterial.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings.

DETAILED DESCRIPTION OF THE INVENTION

Various examples of embodiments of the present invention will be explained in more detail by virtue of the following embodiments illustrated in the figures and/or described below.

Figure 1:
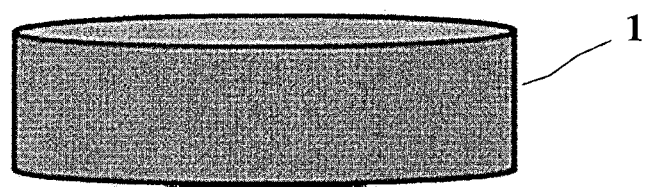
FIG. 1: Bacterially synthesized nanocellulose (BNC) featuring a plurality of different bacterial cellulose networks that form a common homogeneous phase system.

FIG. 1 shows bacterially synthesized nanocellulose (BNC biomaterial) that, according to the invention, consists of a plurality of different bacterial cellulose networks, of which two are shown for illustration only and without wishing to be limited in any way, forming a common phase system of one combined homogeneous phase (reference number 1—combined homogeneous phase).

This exemplary, illustrative phase system is synthesized from two kinds of *Gluconacetobacter* strains, in the example ATCC 23769 and DSM 11804, in a not shown cultivation vessel with a synthesis area of 7 cm². However, the area can be freely selected for the special phase formation in this embodiment. Also optionally any suitable *Gluconacetobacter* strain may be used, including but not limited to ATCC 10245, ATCC 23769, DSM 11804 and DSM 14666.

After separate preparation the two bacterial strains were added together into the cultivation vessel and thus they were inoculated for co-synthesis. An added cultivation medium included a carbon source (preferentially different sugars and their derivatives), a nitrogen source (preferentially peptone) and, if required, a buffer system (preferentially disodium hydrogen phosphate and citric acid). The biosynthesis was carried out at a temperature ranging from 28 to 30° C. during a period from 3 to 21 days and it was tested for both a discontinuous and a continuous synthesis procedure.

A very stable and transparent combined homogenous BNC phase system (see FIG. 1) of the two synthesized BNC networks was reliably obtained with exemplary volume ratios of 5:1 and 2:1 of the culture medium and the bacterial strains, defining an optional range of from 5:1 to 2:1 of the culture medium and bacterial strains.

The inoculation ratio is the volume ratio of the inoculated strains to each other. For example an inoculation ratio of 80:20 means that the volume of one strain used for inoculation was four times higher as compared to the volume of the other strain used for inoculation.

The inoculation ratio is 50:50 (ATCC 23769:DSM 11804), i.e. the quantities of the bacterial strains that take part in the synthesis are identical. A change of this inoculation ratio would additionally allow the control of the pore system and thus of the stability as well as of the transparency of the homogenous BNC biomaterial. With an inoculation ratio of 10:90, for example, a solid/stable, transparent and simultaneously elastic BNC carded web was generated. If the inoculation ratio is reversed (e.g. 90:10), both the strength and the elasticity can be reduced without changing the transparency.

Furthermore, the optional addition of glacial acetic acid in an amount of up to 2% volume/volume can improve the homogeneity of the generated BNC material.

Figure 4A:
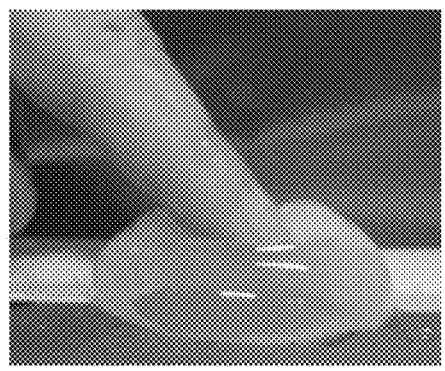
FIGS. 4A and 4B show images of BNC prepared as described with regard to FIG. 1, in which the BNC features two different individual cellulose networks that form a common homogeneous phase.
Figure 4B:
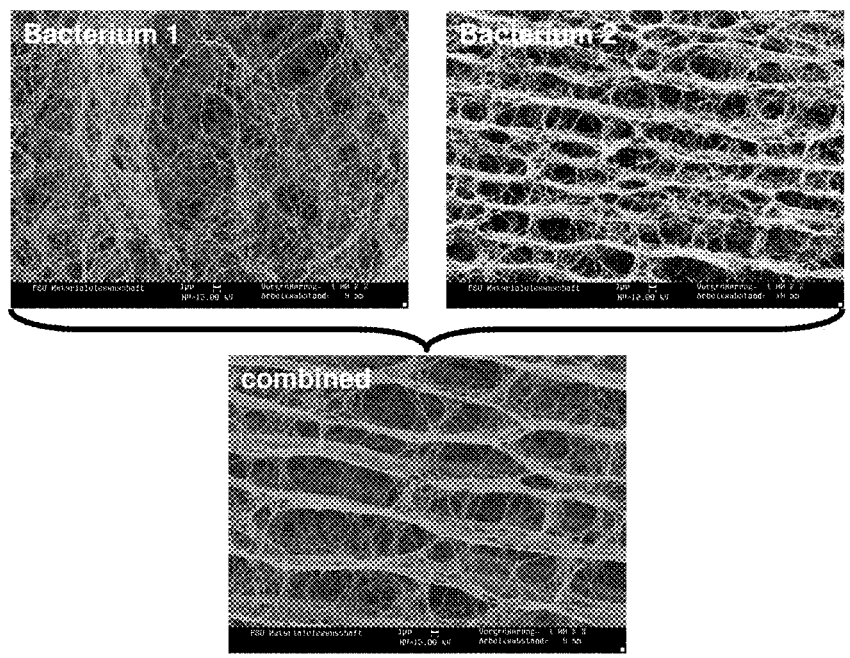

FIGS. 4A and 4B show images of BNC prepared as described with regard to FIG. 1, in which the BNC features two different individual cellulose networks that form a common homogeneous phase. FIG. 4A shows a photograph of actual BNC material, shown with a human hand for scale, indicating the flexibility of the material. FIG. 4B shows electron micrographs of the structure of the material.

Figure 2:
FIG. 2: BNC featuring two different bacterial cellulose networks each of them forming a separate layered single phase.

FIG. 2 shows a BNC material that, as proposed, also features two different bacterial cellulose networks which, however, have been synthesized to a layered phase system comprising separate single phases 2, 3. Each of the separate single phases 2, 3 corresponds to one BNC carded web and its properties known per se and are firmly combined with each other.

This phase system was synthesized from two kinds of *Gluconacetobacter* strains, ATCC 10245 and DSM 14666 in this example, in the cultivation vessel that was mentioned in the first example and that has a synthesis area that can be freely selected for this special phase formation. In this embodiment, the two bacterial strains are separately prepared, too, and are added together into the cultivation vessel for co-synthesis. The added cultivation medium again features a carbon source (preferentially different sugars and their derivatives), a nitrogen source (preferentially peptone), a vitamin source (preferentially yeast extract) and, if required, a buffer system (preferentially disodium hydrogen phosphate and citric acid).

Biosynthesis was performed at a temperature ranging from 28 to 30° C. during a period from 3 to 21 days and was tested with both a discontinuous and continuous synthesis procedure. During the procedure, a stable layered system was obtained from the two separated but firmly combined single phases 2, 3 with a volume ratio of 20:1 between the cultivation medium and the mentioned bacterial strains. Also the *Gluconacetobacter* strains were different from the ones used in the first embodiment, in that in the first embodiment, ATCC 23769 and DSM 11804 were used. In contrast, in the second embodiment, ATCC 10245 and DSM 14666 were used. In the material produced according to this second embodiment, the single phases 2, 3 were externally almost not visible as separate layers. Thus, the synthesized BNC biomaterial visually appears to be a homogenous carded web but structurally features the two different bacterial cellulose networks.

The selected inoculation ratio between the bacterial strains used was 50:50 (ATCC 10245:DSM 14666). If this ratio is changed in favor of one bacterium, the thickness of the single phases 2 or 3 and the resulting properties (water absorption and water retention, etc.) can be specifically controlled. Furthermore, an inoculation ratio of 70:30 between the strains (the volume ratio of 20:1 between the cultivation medium and the bacterial strains was maintained) resulted in an improved transparency without a change of the thickness of the BNC carded web (data not shown).

FIG. 3 shows a BNC that again features two different bacterial cellulose networks which, however, have been synthesized to form a special layered phase system. In this system the two separate single phases (2, 3) were combined via a combined homogenous phase (1). This special phase system was synthesized from the two *Gluconacetobacter* strains ATCC 23769 and DSM 14666, again in the previously mentioned but not shown cultivation vessel, again with a synthesis area of 7 cm². If this synthesis area is changed, the formation of the single phases 2, 3 can be deliberately influenced as follows. Increasing the area (with an inoculation ratio of 50:50) supports the formation of the single phase 2 (corresponding to the bacterial strain DSM 14666) more than the formation of the single phase 3 (corresponding to bacterial strain ATCC 23769).

Figure 3:
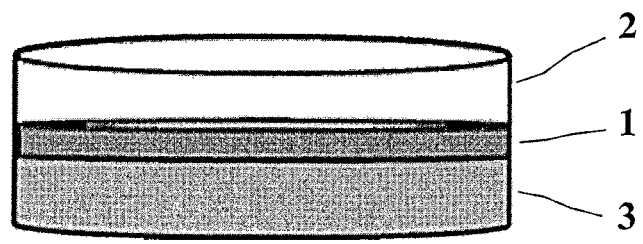
FIG. 3: BNC with two different bacterial cellulose networks that form a layered phase system featuring two layered single phases and one combined, homogeneous phase.

The phase system of the BNC biomaterial shown in FIG. 3 is achieved by the use of the bacterial strains mentioned before and by their separate preparation and subsequent common inoculation. However, a common cultivation of these bacterial strains, common preparation included, would generate a combined homogeneous phase system as shown in FIG. 1.

The cultivation medium used here was again a mixture of a carbon source (preferentially different sugars and their derivatives), a nitrogen source (preferentially peptone), a vitamin source (preferentially yeast extract) and, if required, a buffer system (preferentially disodium hydrogen phosphate and citric acid). The biosynthesis was carried out at a temperature ranging from 28 to 30° C. during a period from 3 to 21 days with a volume ratio of 20:1 between the cultivation medium and the bacterial strains and was tested both for a discontinuous and continuous synthesis procedure.

The inoculation ratio of 50:50 between the bacterial strain led to the externally visible layered BNC phase system (FIG. 3) comprising the aforementioned two single phases 2, 3 and the homogenous phase 1 located between them. Moreover, with this inoculation ratio the proportions of the single phases are identical. The change of the inoculation ratio in favor of one bacterial strain allows the deliberate control of the thickness of the single phases 2, 3 and of the resulting properties (water absorption and water retention, etc.).

Figure 5A:
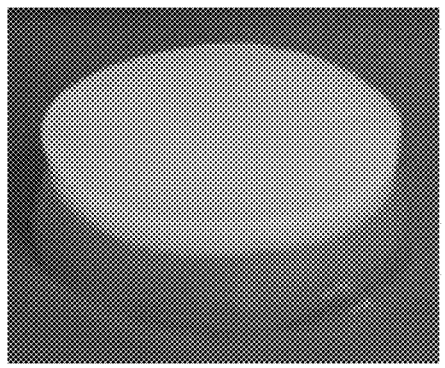
FIGS. 5A and 5B show images of BNC prepared as described with regard to FIG. 3, in which the BNC features two different bacterial cellulose networks that form a layered phase system of two layered single phases and one combined homogeneous phase.
Figure 5B:
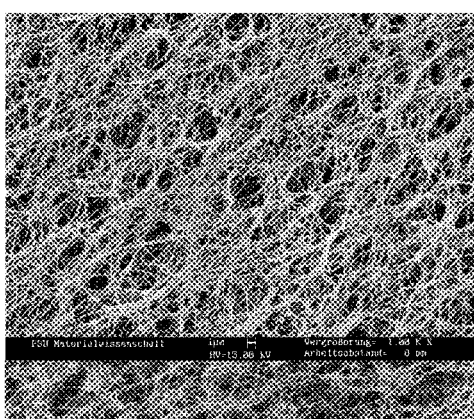
Figure 5B:
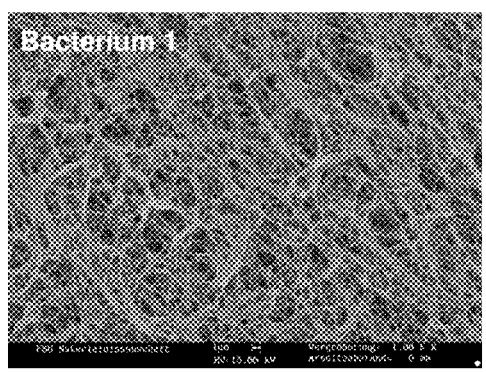
Figure 5B:
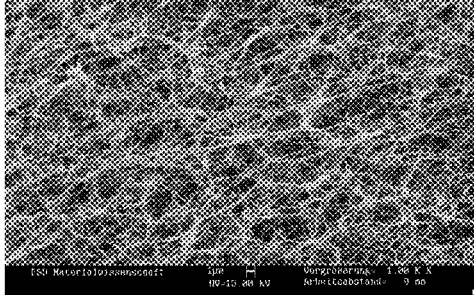
Figure 5B:
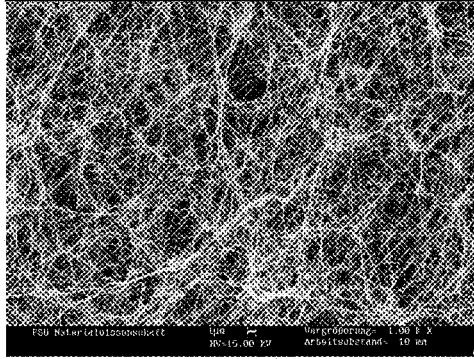
Figure 5B:
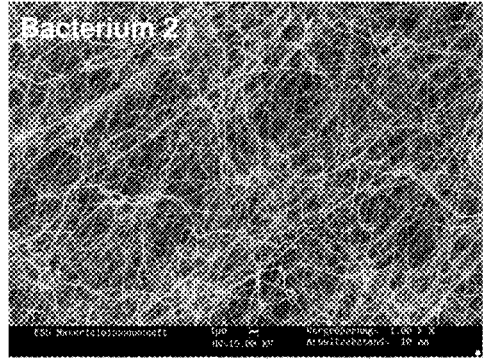

FIGS. 5A and 5B show images of BNC prepared as described with regard to FIG. 3, in which the BNC features two different bacterial cellulose networks that form a layered phase system of two layered single phases and one combined homogeneous phase. FIG. 5A shows a photograph of actual BNC material. FIG. 5B shows electron micrographs of the structure of the material, with the phases labeled. Bacterial strain one is shown at the top right while strain two is shown at the lower right (ATCC 23769 and DSM 14666, respectively).

In order to obtain the multi-phase biomaterials, preferably suitable cellulose-producing bacterial strains are selected for conjoint cultivation (co-cultivation). According to at least some embodiments of the present invention, two or more different cellulose-producing bacterial strains are co-cultivated in order to obtain the inventive multi-phase biomaterials comprising at least two different BNC networks. Preferably, the two or more different cellulose-producing bacterial strains are *Gluconacetobacter* strains. Notably, the international nomenclature has been recently amended and "*Gluconacetobacter*" has been renamed to "*Komagataeibacter*". Preferably, the two or more different cellulose-producing bacterial strains are selected from the group consisting of ATCC 10245, ATCC 23769, DSM 11804 and DSM 14666.

In a preferred embodiment, two cellulose-producing bacterial strains are co-cultivated in order to obtain multi-phase biomaterials comprising exactly two different BNC networks. Preferably, ATCC 23769 is co-cultivated with DSM 11804 or with DSM 14666. Preferably, ATCC 10245 is co-cultivated with DSM 14666.

As described above and also shown in FIGS. 1 to 3, in different embodiments of the present invention, the at least two different bacterial cellulose networks may optionally be formed as a combined homogeneous phase system, as a layered phase system comprising firmly combined separate single phases or as a layered phase system comprising at least one combined homogeneous phase and at least one single phase. The particular phase system formed depends mainly on the kinetics of cellulose production of the different cellulose-producing bacterial strains. For example, if bacterial strains with comparable kinetics of cellulose production are used, the resulting different bacterial cellulose networks are formed as a combined homogeneous phase system. In contrast, if one strain with fast kinetics of cellulose production is combined with a strain with slow kinetics of cellulose production it might be that the slow strain starts production of cellulose only when the fast strain has already substantially finished production of cellulose. In such a case, the different bacterial cellulose networks are formed as a layered phase system comprising firmly combined separate single phases. If the slow strain starts production of cellulose when the fast strain is still producing cellulose, the different bacterial cellulose networks are formed as a layered phase system comprising at least one combined homogeneous phase and at least one single phase. If in such a case the slow strain continues cellulose production when the fast strain has stopped to produce cellulose, the different bacterial cellulose networks are formed as a layered phase system comprising a combined homogeneous phase and two single phases as shown in FIG. 3.

In a preferred embodiment of the present invention, two cellulose-producing bacterial strains are co-cultivated, whose initial kinetics of cellulose production are so similar that the quotient of the initial kinetics of cellulose production of the strain with the faster initial kinetics (dividend) and the initial kinetics of cellulose production of the strain with the slower initial kinetics (divisor) is at most 2, more preferably at most 1.5, more preferably at most 1.2. According to this embodiment, multi-phase biomaterials may be obtained that comprise two different bacterial cellulose networks that are formed as a combined homogeneous phase system.

In another embodiment of the present invention, two cellulose-producing bacterial strains are co-cultivated, whose initial kinetics of cellulose production are so different that the quotient of the initial kinetics of cellulose production of the strain with the faster initial kinetics (dividend) and the initial kinetics of cellulose production of the strain with the slower initial kinetics (divisor) is at least 2.5, more preferably at least 3, more preferably at least 5, more preferably at least 10. According to this embodiment, multi-phase biomaterials may be obtained that comprise two different bacterial cellulose networks that are formed as a layered phase system.

Preferably, the initial kinetics of cellulose production of a cellulose-producing bacterial strain are determined as the weight of cellulose produced by such bacterial strain within 96 hours after beginning of cultivation, more preferably within 72 hours after beginning of cultivation, more preferably within 48 hours after beginning of cultivation, more preferably within 24 hours after beginning of cultivation, more preferably within 12 hours after beginning of cultivation.

The co-cultivated cellulose-producing bacterial strains may also differ in the maximum bacterial cell number that is reached during cultivation. According to at least one embodiment of the present invention, the maximum bacterial cell number of the fast growing strain that is reached during cultivation is preferably higher by a factor of between about 5 to about 15, more preferably by a factor of about 10, in comparison to the maximum bacterial cell number of the slow growing strain that is reached during cultivation.

The properties of the obtained multi-phase biomaterials may optionally be influenced by the inoculation ratio.

Preferably, comparable volumes of the different cellulose-producing strains are used for inoculation. Thus, the inoculation ratio is preferably at most 90:10 and at least 10:90, more preferably at most 80:20 and at least 20:80, more preferably at most 70:30 and at least 30:70, more preferably at most 60:40 and at least 40:60, even more preferably about 50:50.

The properties of the obtained multi-phase biomaterials may also be influenced by the volume ratio of the culture medium to the bacterial strains used for inoculation. Preferably, the volume ratio is at least 2:1, more preferably at least 5:1, more preferably at least 10:1, more preferably at least 15:1. Preferably, the volume ratio is at most 50:1, more preferably at most 30:1, more preferably at most 20:1.

The properties of the obtained multi-phase biomaterials may also be influenced by the composition of the culture medium. Preferably, the culture medium comprises a carbon source, a nitrogen source and a vitamin source and optionally a buffer system. Preferably, the carbon source is selected from different sugars and their derivatives. Preferably, the nitrogen source is peptone. Preferably, the vitamin source is yeast extract. Preferably, the buffer system is disodium hydrogen phosphate and citric acid.

Preferably, the culture medium is liquid.

Preferably, the culture medium comprises the carbon source in an amount of least 10 g/l, more preferably at least 15 g/l based on the volume of the culture medium. Preferably, the culture medium comprises the carbon source in an amount of at most 30 g/l, more preferably at most 25 g/l based on the volume of the culture medium.

Particularly preferably, the culture medium comprises the carbon source in an amount of about 20 g/l.

Preferably, the culture medium comprises the nitrogen source in an amount of least 2 g/l, more preferably at least 4 g/l based on the volume of the culture medium. Preferably, the culture medium comprises the nitrogen source in an amount of at most 10 g/l, more preferably at most 7 g/l based on the volume of the culture medium. Particularly preferably, the culture medium comprises the nitrogen source in an amount of about 5 g/l.

Preferably, the culture medium comprises the vitamin source in an amount of least 2 g/l, more preferably at least 4 g/l based on the volume of the culture medium. Preferably, the culture medium comprises the vitamin source in an amount of at most 10 g/l, more preferably at most 7 g/l based on the volume of the culture medium. Particularly preferably, the culture medium comprises the vitamin source in an amount of about 5 g/l.

Preferably, the culture medium comprises the buffer system in an amount of least 2 g/l, more preferably at least 4 g/l based on the volume of the culture medium. Preferably, the culture medium comprises the buffer system in an amount of at most 10 g/l, more preferably at most 5 g/l based on the volume of the culture medium. Particularly preferably, the culture medium comprises the buffer system in an amount of about 4.5 g/l.

Particularly preferably, the culture medium comprises 20 g/l glucose, 5 g/l peptone, 5 g/l yeast extract, 3.4 g/l disodium hydrogen phosphate and 1.15 g/l citric acid.

The properties of the obtained multi-phase biomaterials may also be influenced by the cultivation temperature. Preferably, the cultivation temperature is at least 20° C., more preferably at least 25° C., more preferably at least 28° C. If the cultivation temperature is too low, the bacterial strains do not grow properly. Preferably, the cultivation temperature is at most 36° C., more preferably at most 33° C., more preferably at most 30° C. If the cultivation temperature is too high, the bacterial strains do not grow properly.

The properties of the obtained multi-phase biomaterials may also be influenced by the cultivation time. Preferably the cultivation time is at least 3 days, more preferably at least 7 days, more preferably at least 10 days. If the cultivation time is too short, not enough cellulose is produced. Preferably, the cultivation time is at most 30 days, more preferably at most 25 days, more preferably at most 20 days. Particularly preferably, the cultivation time is about 14 days.

The properties of the obtained multi-phase biomaterials may also be influenced by the culture volume. Preferably, the culture volume is at least 20 ml, more preferably at least 500 ml, more preferably at least 2000 ml. Preferably, the culture volume is at most 200 l, more preferably at most 180 l, more preferably at most 100 l.

The properties of the obtained multi-phase biomaterials may also be influenced by the cultivation vessel. Preferably, the cultivation vessel has a synthesis area of at least 1 $cm^2$, more preferably at least 10 $cm^2$, more preferably at least 100 $cm^2$. Preferably, the cultivation vessel has a synthesis area of at most 50,000 $cm^2$, more preferably at most 20,000 $cm^2$, more preferably at most 1,000 $cm^2$. Particularly preferably, the cultivation vessel has a synthesis area of about 7 $cm^2$.

As described above, the present invention relates to multi-phase biomaterials comprising at least two different BNC networks. Even if the different BNC networks are synthesized as a combined homogeneous phase according to one embodiment of the present invention, the different networks may be intertwined but they still remain their individual molecular and supra-molecular structure. Preferably, the multi-phase biomaterials comprise exactly two different BNC networks.

As also described above, the multi-phase biomaterial of the present invention can be obtained by conjoint cultivation of at least two different cellulose-producing bacterial strains. Importantly, not every biomaterial resulting from a combination of two different bacterial species is necessarily a multi-phase material comprising two different BNC networks. Rather, generally no multi-phase materials are produced because the cellulose fibers are simultaneously generated and modified by both bacterial strains so that a single hybrid network is produced, which is homogeneous on both macroscopic and molecular level. Furthermore, in the predominant number of cases, conjoint cultivation of two different cellulose-producing bacterial strains results in cellulose materials characterized by the properties of only one strain because the more dominant strain will suppress the other strain as can be seen from the following comparative examples, in which strains were combined that are not preferred for combination according to the present invention.

Two *Gluconacetobacter* strains ("*Komagataeibacter*" according to new nomenclature) were co-cultivated in each of comparative example 1 and comparative example 2. In comparative example 1 ATCC 23769 and ATCC 10245 were used. In comparative example 2, ATCC10245 and ATCC 53582 were used. The conjoint cultivation was done in Sueoka's high salt medium (HSM medium (pH 6), Sueoka, N. (1960) *Proc. Natl. Acad. Sci. USA* 46, 83-91) in a cultivation vessel with a synthesis area of 7 $cm^2$. The total volume of the inoculated medium was 40 ml. Separate pre-cultures of the two bacterial strains were added together into the cultivation vessel and thus they were inoculated for co-synthesis. The ratio of the culture medium to the pre-cultures of the bacterial strains was 20:1. The inoculation ratio was 50:50 in both comparative examples, i.e. the quantities of the bacterial strains that take part in the synthesis were identical in each case.

The biosynthesis was carried out at a temperature of 28° C. during a period of 14 days. It was found that neither the biomaterial obtained by combining ATCC 23769 and ATCC 10245 according to comparative example 1, nor the biomaterial obtained by combining ATCC10245 and ATCC 53582 according to comparative example 2, was a multi-phase biomaterial comprising at least two different bacterial cellulose networks. Instead, the bacterial cellulose was built only by the dominant strain.

In contrast, a multi-phase biomaterial comprising two different bacterial cellulose networks was obtained according to example 1 that was performed as described above, except that the two *Gluconacetobacter* strains ("*Komagataeibacter*" according to the new nomenclature) that are preferred for co-cultivation were used. In example 1 ATCC 23769 and DSM 11804 were used. The conjoint cultivation was done in HSM medium in a cultivation vessel with a synthesis area of 7 $cm^2$ as described above. The total volume of the inoculated medium was 40 ml. Separate pre-cultures of the two bacterial strains were added together into the cultivation vessel and thus they were inoculated for co-synthesis. The volume ratio of the culture medium to the pre-cultures of the bacterial strains was 5:1. The inoculation ratio was 20:80 (ATCC 23769:DSM 11804). The biosynthesis was carried out at a temperature of 28° C. during a period of 14 days. A transparent multi-phase biomaterial comprising two different bacterial cellulose networks was obtained.

As noted above, a wound dressing according to various embodiments of the present invention preferably comprises the biomaterials as described herein. Such wound dressings may optionally be transparent, due to the combined homogeneous phase system as shown in FIG. 1. The transparency of the wound dressings enables visual inspection of the wound by the doctor without the need to remove the protective wound dressing. A wound dressing comprising such biomaterials may optionally remain transparent even at much greater thickness, which in turn enables production of wound dressings with significantly increased solid content by removal of liquid; that is, the percentage of the wound dressing material that comprises solids may optionally be much higher than for other biomaterials. The wound dressings become thinner by removal of water. However, as the BNC biomaterials as described herein are thicker than is known in the art, the decrease in thickness due to liquid removal still leaves a reasonable thickness for the wound dressing. In contrast, the transparent wound dressings that are known in the art are so thin, that the content of solids may not be increased by removal of water as the resulting BNC materials would be too thin for use as wound dressings. Thus, transparent wound dressings of increased content of solids have been provided by the present invention.

Without wishing to be limited to a closed list, the increased content of solids is particularly advantageous for wound dressings that are used for covering severe burns (second and especially third degree burns). Such burns produce a high amount of exudates that need to be absorbed by the wound dressings. Higher content of solids of a wound dressing results in increased absorptive properties of the wound dressing. Consequently, the wound dressings as described herein that have an increased solids content need to be exchanged substantially less often so that the wound is protected for an increased length of time before the protective cover needs to be removed.

These desirable properties are obtained by selecting and combining two or more cellulose-producing bacterial strains, thereby enabling exploitation of properties of BNC from strains that was not possible if those strains were cultivated alone. Some strains do produce BNC that does not have the mechanical strength necessary for the above application, other applications as described herein or otherwise. However, they might contribute to transparency or absorption properties in an advantageous manner. Therefore, the combination of such a strain with a strain that produces BNC with advantageous mechanical properties results in BNC biomaterial that combines the positive aspects of both BNCs.

While the invention has been described with respect to a limited number of embodiments, it will be appreciated that many variations, modifications and other applications of the invention may be made, and that various combinations and subcombinations of embodiments are also possible and encompassed within the scope of this application.

What is claimed is:

1. A multi-phase biomaterial, comprising bacterially synthesized nanocellulose (BNC) comprising a plurality of different bacterial cellulose networks arranged in a plurality of phases, wherein the plurality of different bacterial cellulose networks are integrally combined in a homogeneous phase system or wherein the plurality of different bacterial cellulose networks are formed as a layered phase system comprising at least one combined homogeneous phase and at least one single phase, wherein said BNC has a transparency to an extent that more than 50% of visible light passes through the biomaterial at a thickness of greater than 2 mm of the biomaterial, and wherein said BNC has a thickness greater than 2 mm.

2. The multi-phase biomaterial of claim 1, wherein the plurality of different bacterial cellulose networks differ in their molecular structure.

3. The multi-phase biomaterial of claim 1, wherein the plurality of different bacterial cellulose networks differ in their supra-molecular structure.

4. The multi-phase biomaterial of claim 1, comprising cellulosic structures on the basis of modified C-sources.

5. The multi-phase biomaterial of claim 4, wherein said C-sources comprise one or both of N-acetyl glucosamine or glucosamine.

6. The multi-phase biomaterial of claim 1, wherein said bacterial cellulose networks are produced by a plurality of different *Gluconacetobacter* strains.

7. The multi-phase biomaterial of claim 6, wherein said strains comprise ATCC 23769 and DSM 11804.

8. The multi-phase biomaterial of claim 1, wherein said BNC has a thickness greater than 5 mm.

9. The multi-phase biomaterial of claim 8, wherein said BNC has a thickness greater than 10 mm.

10. The multi-phase biomaterial of claim 9, wherein said BNC has a thickness greater than 20 mm.

11. The multi-phase biomaterial of claim 10, wherein said BNC has a thickness greater than 30 mm.

12. The multi-phase biomaterial of claim 11, wherein said BNC has a thickness greater than 50 mm.

13. A wound dressing, comprising the multi-phase biomaterial of claim 8.

14. The multi-phase biomaterial of claim 1, wherein said BNC has solids content of at least 5%.

15. The multi-phase biomaterial of claim 14, wherein said BNC has solids content of at least 6%.

16. The multi-phase biomaterial of claim 15, wherein said BNC has solids content of at least 8%.

17. The multi-phase biomaterial of claim 16, wherein said BNC has solids content of at least 10%.

18. The multi-phase biomaterial of claim 17, wherein said BNC has solids content of at least 15%.

19. The multi-phase biomaterial of claim 1, wherein said BNC has a tensile strength in the native wet state of at least 0.1 MPa.

20. The multi-phase biomaterial of claim 19, wherein said BNC has a tensile strength in the native wet state of at least 0.15 MPa.

21. The multi-phase biomaterial of claim 20, wherein said BNC has a tensile strength in the native wet state of at least 0.2 MPa.

22. The multi-phase biomaterial of claim 21, wherein said BNC has a tensile strength in the native wet state of at most 0.9 MPa.

23. The multi-phase biomaterial of claim 22, wherein said BNC has a tensile strength in the native wet state of at most 0.7 MPa.

24. The multi-phase biomaterial of claim 23, wherein said BNC has a tensile strength in the native wet state of at most 0.5 MPa.

25. The multi-phase biomaterial of claim 21, wherein said BNC has a tensile strength in the native wet state of from 0.2 MPa to 0.5 MPa.

26. The multi-phase biomaterial of claim 19, wherein said BNC has a water absorption capacity (WAC) of at least 80%.

27. The multi-phase biomaterial of claim 26, wherein said BNC has a water absorption capacity (WAC) of at least 120%.

28. The multi-phase biomaterial of claim 27, wherein said BNC has a water absorption capacity (WAC) of at least 150%.

29. The multi-phase biomaterial of claim 26, wherein said BNC has a water absorption capacity (WAC) of at most 300%.

30. The multi-phase biomaterial of claim 29, wherein said BNC has a water absorption capacity (WAC) of at most 250%.

31. The multi-phase biomaterial of claim 30, wherein said BNC has a water absorption capacity (WAC) of at most 200%.

32. The multi-phase biomaterial of claim 28, wherein said BNC has a water absorption capacity (WAC) of from 150% to 200%.

33. The multi-phase biomaterial of claim 26, wherein said BNC has a moist vapor transmission rate in the wet state of at least 100 g/(m2*24 h).

34. The multi-phase biomaterial of claim 33, wherein said BNC has a moist vapor transmission rate in the wet state of at least 200 g/(m2*24 h).

35. The multi-phase biomaterial of claim 34, wherein said BNC has a moist vapor transmission rate in the wet state of at least 500 g/(m2*24 h).

36. The multi-phase biomaterial of claim 35, wherein said BNC has a moist vapor transmission rate in the wet state of at most 3000 g/(m2*24 h).

37. The multi-phase biomaterial of claim 36, wherein said BNC has a moist vapor transmission rate in the wet state of at most 2000 g/(m2*24 h).

38. The multi-phase biomaterial of claim 37, wherein said BNC has a moist vapor transmission rate in the wet state of at most 1000 g/(m2*24 h).

39. The multi-phase biomaterial of claim 35, wherein said BNC has a moist vapor transmission rate in the wet state of from 500 g/(m2*24 h) to 1000 g/(m2*24 h).

40. The multi-phase biomaterial of claim 1, wherein the plurality of different BNC networks differ in their molecular structure according to at least one of degree of polymerization ($DP_n$), polydispersity index (PDI) or both.

41. The multi-phase biomaterial of claim 40, wherein at least one BNC network is characterized by a $DP_n$ of at least 4000.

42. The multi-phase biomaterial of claim 41, wherein at least one BNC network is characterized by a $DP_n$ of at least 6000.

43. The multi-phase biomaterial of claim 42, wherein at least one BNC network is characterized by a $DP_n$ of at least 8000.

44. The multi-phase biomaterial of claim 40, wherein at least one BNC network is characterized by a $DP_n$ of at most 2000.

45. The multi-phase biomaterial of claim 44, wherein at least one BNC network is characterized by a $DP_n$ of at most 1000.

46. The multi-phase biomaterial of claim 45, wherein at least one BNC network is characterized by a $DP_n$ of at most 500.

47. The multi-phase biomaterial of claim 40, wherein a first BNC network has a higher $DP_n$ and a second BNC network has a lower $DP_n$, wherein the $DP_n$ of the first BNC network is higher by a factor of at least 2.

48. The multi-phase biomaterial of claim 47, wherein the $DP_n$ of the first BNC network is higher by a factor of at least 5.

49. The multi-phase biomaterial of claim 40, wherein at least one BNC network is characterized by a PDI of at least 1.5.

50. The multi-phase biomaterial of claim 49, wherein at least one BNC network is characterized by a PDI of at least 1.7.

51. The multi-phase biomaterial of claim 50, wherein at least one BNC network is characterized by a PDI of at least 2.0.

52. The multi-phase biomaterial of claim 51, wherein at least one BNC network is characterized by a PDI of at most 8.

53. The multi-phase biomaterial of claim 52, wherein at least one BNC network is characterized by a PDI of at most 6.

54. The multi-phase biomaterial of claim 53, wherein at least one BNC network is characterized by a PDI of at most 4.

55. The multi-phase biomaterial of claim 40, wherein a first BNC network has a higher PDI and a second BNC network has a lower PDI, wherein the PDI of the first BNC network is higher by a factor of at least 1.5.

56. The multi-phase biomaterial of claim 55, wherein the PDI of the first BNC network is higher by a factor of at least 2.

57. The multi-phase biomaterial of claim 55, wherein the PDI of the first BNC network is higher by a factor of at least 3.

58. The multi-phase biomaterial of claim 40, wherein a first BNC network has a higher PDI and a lower $DP_n$ as compared to a second BNC network.

59. The multi-phase biomaterial of claim 1, wherein the plurality of different BNC networks differ in their degree of crystallinity.

60. The multi-phase biomaterial of claim 59, wherein at least one BNC network is characterized by a degree of crystallinity of at least 55%.

61. The multi-phase biomaterial of claim 60, wherein at least one BNC network is characterized by a degree of crystallinity of at least 60%.

62. The multi-phase biomaterial of claim 61, wherein at least one BNC network is characterized by a degree of crystallinity of at least 65%.

63. The multi-phase biomaterial of claim 59, wherein a plurality of BNC networks of the multi-phase biomaterials have a degree of crystallinity of at most 95%.

64. The multi-phase biomaterial of claim 63, wherein a plurality of BNC networks of the multi-phase biomaterials have a degree of crystallinity of at most 80%.

65. The multi-phase biomaterial of claim 63, wherein a plurality of BNC networks of the multi-phase biomaterials have a degree of crystallinity of at most 70%.

66. The multi-phase biomaterial of claim 59, wherein a degree of crystallinity of a first BNC network with a highest degree of crystallinity of said plurality of BNC networks is higher by a factor of at least 1.2 than a degree of crystallinity of a second BNC network with a lowest degree of crystallinity of said plurality of BNC networks.

67. The multi-phase biomaterial of claim 66, wherein said factor is at least 1.5.

68. The multi-phase biomaterial of claim 67, wherein said factor is at least 2.

69. The multi-phase biomaterial of claim 1, wherein said plurality of different BNC networks comprise a plurality of different thicknesses of microfibrils.

70. The multi-phase biomaterial of claim 1, wherein said plurality of different BNC networks comprise a plurality of different pore sizes, determined as an average cross sectional area of pores of said networks.

71. The multi-phase biomaterial of claim 70, wherein at least one BNC network is characterized by an average cross sectional pore area of at least 15 $\mu m^2$.

72. The multi-phase biomaterial of claim 71, wherein at least one BNC network is characterized by an average cross sectional pore area of at least 20 $\mu m^2$.

73. The multi-phase biomaterial of claim 72, wherein at least one BNC network is characterized by an average cross sectional pore area of at least 25 $\mu m^2$.

74. The multi-phase biomaterial of claim 70, wherein a plurality of BNC networks of the multi-phase biomaterials have an average cross sectional pore area of at most 50 $\mu m^2$.

75. The multi-phase biomaterial of claim 74, wherein a plurality of BNC networks of the multi-phase biomaterials have an average cross sectional pore area of at most 40 $\mu m^2$.

76. The multi-phase biomaterial of claim 75, wherein a plurality of BNC networks of the multi-phase biomaterials have an average cross sectional pore area of at most 30 $\mu m^2$.

77. The multi-phase biomaterial of claim 70, wherein an average cross sectional pore area of a first BNC network is higher by a factor of at least 1.2 than for a second BNC network.

78. The multi-phase biomaterial of claim 77, wherein said average cross sectional pore area is at least 1.5 times greater.

79. The multi-phase biomaterial of claim 78, wherein said average cross sectional pore area is at least 2 times greater.

80. A method for producing multi-phase biomaterials comprised of bacterially synthesized nanocellulose (BNC), comprising inoculating a culture medium with at least two different cellulose-producing bacterial strains, which have been commonly or separately prepared, thereby to synthesize BNC comprised of a plurality of different bacterial cellulose networks wherein BNC structure and BNC properties of the multi-phase biomaterials are predetermined by selection of the at least two different bacterial strains, by their preparation and inoculation and by selection of conditions of the synthesis, wherein said BNC has a transparency to an extent that more than 50% of visible light passes through the biomaterial at a thickness greater than 2 mm of the biomaterial, and wherein said BNC has thickness greater than 2 mm.

81. The method of claim 80, wherein the at least two different bacterial cellulose networks are prepared independently from each other and subsequently combined and commonly synthesized.

82. The method of claim 80, wherein the at least two different bacterial cellulose networks are combined for co-synthesis already before the inoculation.

83. The method of claim 80, wherein said bacterial strains are selected to generate cellulose-like structures on the basis of modified C-sources.

84. The method of claim 83, wherein said C-sources are selected from the group consisting of N-acetyl glucosamine and glucosamine.

85. The method of claim 80, wherein said plurality of different bacterial strains comprise a plurality of different *Gluconacetobacter* strains.

86. The method of claim 85, wherein said strains comprise ATCC 23769 and DSM 11804.

* * * * *